(12) United States Patent
Renock (10) Patent No.: US 12,427,099 B2
(45) Date of Patent: *Sep. 30, 2025

(54) PERSONAL CARE COMPOSITION

(71) Applicant: The Procter & Gamble Company, Cincinnati, OH (US)

(72) Inventor: Sean Michael Renock, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/529,427

(22) Filed: Nov. 18, 2021

(65) Prior Publication Data

US 2022/0160606 A1 May 26, 2022

Related U.S. Application Data

(60) Provisional application No. 63/151,851, filed on Feb. 22, 2021, provisional application No. 63/117,064, filed on Nov. 23, 2020.

(51) Int. Cl.
| | |
|---|---|
| *A61K 8/58* | (2006.01) |
| *A61K 8/36* | (2006.01) |
| *A61K 8/37* | (2006.01) |
| *A61K 8/42* | (2006.01) |
| *A61K 8/49* | (2006.01) |
| *A61K 8/73* | (2006.01) |
| *A61Q 5/00* | (2006.01) |

(52) U.S. Cl.
CPC ............... *A61K 8/58* (2013.01); *A61K 8/361* (2013.01); *A61K 8/375* (2013.01); *A61K 8/42* (2013.01); *A61K 8/4926* (2013.01); *A61K 8/737* (2013.01); *A61Q 5/006* (2013.01)

(58) Field of Classification Search
CPC .......... A61K 8/58; A61K 8/361; A61K 8/375; A61K 8/42; A61K 8/4926; A61K 8/737; A61Q 6/006
See application file for complete search history.

(56) References Cited

U.S. PATENT DOCUMENTS

| | | |
|---|---|---|
| 1,489,388 A | 4/1924 | Glenn |
| 1,600,340 A | 9/1926 | Hoffman |
| 1,612,255 A | 12/1926 | William |
| 2,438,091 A | 3/1948 | Lynch |
| 2,528,378 A | 10/1950 | Mannheimer |
| 2,658,072 A | 11/1953 | Milton |
| 2,809,971 A | 10/1957 | Jack et al. |
| 2,879,231 A | 3/1959 | Marshall |
| 3,219,656 A | 11/1965 | Boettner |
| 3,236,733 A | 2/1966 | Karsten et al. |
| 3,373,208 A | 3/1968 | Blumenthal |
| 3,636,113 A | 1/1972 | Hall |
| 3,709,437 A | 1/1973 | Wright |
| 3,716,498 A | 2/1973 | Hall |
| 3,753,196 A | 8/1973 | Kurtz et al. |
| 3,761,418 A | 9/1973 | Parran |
| 3,792,068 A | 2/1974 | Luedders et al. |
| 3,887,692 A | 6/1975 | Gilman |
| 3,904,741 A | 9/1975 | Jones et al. |
| 3,950,532 A | 4/1976 | Bouillon et al. |
| 3,958,581 A | 5/1976 | Abegg et al. |
| 3,959,160 A | 5/1976 | Horsler et al. |
| 3,962,418 A | 6/1976 | Birkofer |
| 4,049,792 A | 9/1977 | Elsnau |
| 4,089,945 A | 5/1978 | Brinkman et al. |
| 4,120,948 A | 10/1978 | Shelton |
| 4,137,180 A | 1/1979 | Naik |
| 4,237,155 A | 12/1980 | Kardouche |
| 4,309,119 A | 1/1982 | Wittersheim |
| 4,323,683 A | 4/1982 | Bolich, Jr. et al. |
| 4,329,334 A | 5/1982 | Su et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,726,945 A | 2/1988 | Patel |
| 4,732,696 A | 3/1988 | Urfer |
| 4,839,166 A | 6/1989 | Grollier et al. |
| 4,854,333 A | 8/1989 | Inman et al. |
| 4,867,971 A | 9/1989 | Ryan et al. |

(Continued)

FOREIGN PATENT DOCUMENTS

| | | |
|---|---|---|
| BE | 825146 A | 8/1975 |
| BR | 199400875 A | 5/1996 |

(Continued)

OTHER PUBLICATIONS

PCT Search Report and Written Opinion for PCT/US2021/059834 dated Mar. 15, 2022, 16 pages.
Acne Foaming Cleanser, Database accession No. 4172863, Jul. 29, 2016, 3 pages.
Naturally Rich Moisturizing Shampoo, Database accession No. 6421011, Mar. 27, 2019, 3 pages.
Shampoo C, Database accession No. 1632217, Sep. 29, 2011, 3 pages.
PubChem CID 3033856 for decyl glucoside. downloaded Jun. 22, 2023, 32 pages. (Year: 2023).
"Comparative Study on the Chemical constituents of Aloe Vera and Aloe Kula in China", Zhang Xiaohua et al., Flavor Cosmetics, No. 63, dated Dec. 31, 2000, pp. 7-11.

(Continued)

*Primary Examiner* — Shobha Kantamneni
(74) *Attorney, Agent, or Firm* — Linda M. Sivik (57) ABSTRACT

A personal care composition exhibiting excellent cleaning qualities without the use, or inclusion, of a sulfated surfactant; while also delivering an anti-dandruff benefit. The personal care composition contains 7% to 12% sodium cocoyl alaninate; 3% to about 10% glyceryl ester; an anti-dandruff agent; a liquid carrier; and wherein the personal care composition is substantially free of sulfated surfactants. The sodium cocoyl alaninate to glyceryl ester ratio can be 2:1. The viscosity of the personal care composition can be 3 mPa-s to 12 Pa-s.

14 Claims, 2 Drawing Sheets

(56) References Cited

U.S. PATENT DOCUMENTS

| | | |
|---|---|---|
| 4,931,274 A | 6/1990 | Barabino et al. |
| 4,973,416 A | 11/1990 | Kennedy |
| 4,985,238 A | 1/1991 | Tanner et al. |
| 4,997,641 A | 3/1991 | Hartnett |
| 5,019,375 A | 5/1991 | Tanner et al. |
| 5,093,112 A | 3/1992 | Birtwistle et al. |
| 5,104,646 A | 4/1992 | Bolich, Jr. |
| 5,106,609 A | 4/1992 | Bolich, Jr. |
| 5,135,747 A | 8/1992 | Faryniarz et al. |
| 5,156,834 A | 10/1992 | Beckmeyer et al. |
| 5,294,644 A | 3/1994 | Login et al. |
| 5,296,157 A | 3/1994 | Macgilp et al. |
| 5,296,622 A | 3/1994 | Uphues |
| 5,298,640 A | 3/1994 | Callaghan et al. |
| 5,332,569 A | 7/1994 | Wood et al. |
| 5,364,031 A | 11/1994 | Taniguchi et al. |
| 5,374,421 A | 12/1994 | Tashiro |
| 5,374,614 A | 12/1994 | Behan et al. |
| 5,409,695 A | 4/1995 | Abrutyn et al. |
| 5,415,810 A | 5/1995 | Lee et al. |
| 5,417,965 A | 5/1995 | Janchitraponvej et al. |
| 5,429,816 A | 7/1995 | Hofrichter et al. |
| 5,439,682 A | 8/1995 | Wivell |
| 5,441,659 A | 8/1995 | Minor |
| 5,486,303 A | 1/1996 | Capeci |
| 5,489,392 A | 2/1996 | Capeci |
| 5,496,488 A | 3/1996 | Kacher et al. |
| 5,516,448 A | 5/1996 | Capeci |
| 5,536,493 A | 7/1996 | Dubief |
| 5,554,588 A | 9/1996 | Behan et al. |
| 5,560,918 A | 10/1996 | Wivell |
| 5,565,422 A | 10/1996 | Del |
| 5,569,645 A | 10/1996 | Dinniwell |
| 5,574,005 A | 11/1996 | Welch |
| 5,576,282 A | 11/1996 | Miracle |
| 5,578,298 A | 11/1996 | Berthiaume |
| 5,595,967 A | 1/1997 | Miracle |
| 5,597,936 A | 1/1997 | Perkins |
| 5,599,549 A | 2/1997 | Wivell |
| 5,624,666 A | 4/1997 | Coffindaffer et al. |
| 5,635,469 A | 6/1997 | Fowler et al. |
| 5,665,267 A | 9/1997 | Dowell et al. |
| 5,691,297 A | 11/1997 | Nassano |
| 5,714,137 A | 2/1998 | Trinh |
| 5,747,436 A | 5/1998 | Patel |
| 5,776,444 A | 7/1998 | Birtwistle et al. |
| 5,800,897 A | 9/1998 | Sharma |
| 5,816,446 A | 10/1998 | Steindorf et al. |
| 5,830,440 A | 11/1998 | Sturla et al. |
| 5,853,618 A | 12/1998 | Barker |
| 5,879,584 A | 3/1999 | Bianchetti |
| 5,891,424 A | 4/1999 | Bretzler et al. |
| 5,902,225 A | 5/1999 | Monson |
| 5,925,603 A | 7/1999 | D'Angelo |
| 5,942,217 A | 8/1999 | Woo et al. |
| 5,976,514 A | 11/1999 | Guskey et al. |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,139,828 A | 10/2000 | Mccullough |
| 6,153,567 A | 11/2000 | Hughes |
| 6,153,569 A | 11/2000 | Halloran |
| 6,162,834 A | 12/2000 | Sebillotte-Arnaud et al. |
| 6,180,121 B1 | 1/2001 | Guenin et al. |
| 6,225,464 B1 | 5/2001 | Hiler, II |
| 6,231,844 B1 | 5/2001 | Nambu |
| 6,232,302 B1 | 5/2001 | Alberico et al. |
| 6,248,135 B1 | 6/2001 | Trinh et al. |
| 6,268,431 B1 | 7/2001 | Snyder et al. |
| 6,284,225 B1 | 9/2001 | Bhatt |
| 6,329,331 B1 | 12/2001 | Aronson |
| 6,335,312 B1 | 1/2002 | Coffindaffer et al. |
| 6,352,688 B1 | 3/2002 | Scavone et al. |
| 6,386,392 B1 | 5/2002 | Argentieri |
| 6,413,920 B1 | 7/2002 | Bettiol |
| 6,423,305 B1 | 7/2002 | Cauwet-Martin et al. |
| 6,436,442 B1 | 8/2002 | Woo et al. |
| 6,451,300 B1 | 9/2002 | Dunlop et al. |
| 6,488,943 B1 | 12/2002 | Beerse et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,656,923 B1 | 12/2003 | Trinh |
| 6,660,288 B1 | 12/2003 | Behan et al. |
| 6,679,324 B2 | 1/2004 | Den et al. |
| 6,716,455 B2 | 4/2004 | Birkel |
| 6,716,805 B1 | 4/2004 | Sherry |
| 6,740,713 B1 | 5/2004 | Busch et al. |
| 6,743,760 B1 | 6/2004 | Hardy et al. |
| 6,764,986 B1 | 7/2004 | Busch et al. |
| 6,767,507 B1 | 7/2004 | Woo et al. |
| 6,794,356 B2 | 9/2004 | Turner |
| 6,814,088 B2 | 11/2004 | Barnabas et al. |
| 6,827,795 B1 | 12/2004 | Kasturi et al. |
| 6,869,923 B1 | 3/2005 | Cunningham |
| 6,897,253 B2 | 5/2005 | Schmucker-castner |
| 6,908,889 B2 | 6/2005 | Niemiec et al. |
| 6,930,078 B2 | 8/2005 | Wells |
| 6,992,054 B2 | 1/2006 | Lee et al. |
| 7,018,978 B2 | 3/2006 | Miracle et al. |
| 7,030,068 B2 | 4/2006 | Clare et al. |
| 7,100,767 B2 | 9/2006 | Chomik et al. |
| 7,151,079 B2 | 12/2006 | Fack et al. |
| 7,172,099 B2 | 2/2007 | Hoefte |
| 7,202,198 B2 | 4/2007 | Gordon et al. |
| 7,217,752 B2 | 5/2007 | Schmucker-Castner et al. |
| 7,220,408 B2 | 5/2007 | Decoster et al. |
| 7,223,361 B2 | 5/2007 | Kvietok |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,598,213 B2 | 10/2009 | Geary et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,841,036 B2 | 11/2010 | Smith |
| 7,867,505 B2 | 1/2011 | Elliott et al. |
| 7,928,053 B2 | 4/2011 | Hecht et al. |
| 7,977,288 B2 | 7/2011 | SenGupta |
| 8,007,545 B2 | 8/2011 | Fujii et al. |
| 8,058,500 B2 | 11/2011 | Sojka et al. |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,158,571 B2 | 4/2012 | Alonso |
| 8,300,949 B2 | 10/2012 | Xu |
| 8,322,631 B2 | 12/2012 | Richardson et al. |
| 8,343,469 B2 | 1/2013 | Bierganns et al. |
| 8,349,300 B2 | 1/2013 | Wells |
| 8,357,359 B2 | 1/2013 | Woo et al. |
| 8,361,450 B2 | 1/2013 | Johnson et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,539,631 B2 | 9/2013 | Catalfamo et al. |
| 8,574,561 B1 | 11/2013 | Patel et al. |
| 8,580,725 B2 | 11/2013 | Kuhlman et al. |

(56) References Cited

U.S. PATENT DOCUMENTS

| | | |
|---|---|---|
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,679,316 B2 | 3/2014 | Brunner et al. |
| 8,680,035 B2 | 3/2014 | Kuhlman et al. |
| 8,699,751 B2 | 4/2014 | Maladen |
| 8,709,337 B2 | 4/2014 | Gruenbacher et al. |
| 8,709,385 B2 | 4/2014 | Tamarkin |
| 8,741,275 B2 | 6/2014 | Dente et al. |
| 8,741,363 B2 | 6/2014 | Albrecht et al. |
| 8,771,765 B1 | 7/2014 | Fernandez |
| 8,772,354 B2 | 7/2014 | Williams et al. |
| 8,795,635 B2 | 8/2014 | Tamarkin et al. |
| 8,877,316 B2 | 11/2014 | Hasenoehrl et al. |
| 8,883,698 B2 | 11/2014 | Scheibel et al. |
| 8,931,711 B2 | 1/2015 | Gruenbacher |
| 8,980,239 B2 | 3/2015 | Staudigel et al. |
| 8,987,187 B2 | 3/2015 | Smets et al. |
| 9,006,162 B1 | 4/2015 | Rizk |
| 9,186,642 B2 | 11/2015 | Dihora et al. |
| 9,187,407 B2 | 11/2015 | Koshti et al. |
| 9,265,727 B1 | 2/2016 | Lowenborg |
| 9,271,908 B2 | 3/2016 | Allef |
| 9,272,164 B2 | 3/2016 | Johnson et al. |
| 9,296,550 B2 | 3/2016 | Smith |
| 9,308,398 B2 | 4/2016 | Hutton et al. |
| 9,393,447 B2 | 7/2016 | Zasloff |
| 9,428,616 B2 | 8/2016 | Wagner |
| 9,511,007 B2 | 12/2016 | Frantz et al. |
| 9,512,275 B2 | 12/2016 | Wagner |
| 9,610,239 B2 | 4/2017 | Feng |
| 9,655,821 B2 | 5/2017 | Carter et al. |
| 9,662,291 B2 | 5/2017 | Johnson et al. |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,949,911 B2 | 4/2018 | Cetti |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,039,706 B2 | 8/2018 | Meralli et al. |
| 10,039,939 B2 | 8/2018 | Xavier et al. |
| 10,113,140 B2 | 10/2018 | Frankenbach |
| 10,182,976 B2 | 1/2019 | Staudigel |
| 10,238,685 B2 | 3/2019 | Dunn et al. |
| 10,265,261 B2 | 4/2019 | Park et al. |
| 10,311,575 B2 | 6/2019 | Stofel |
| 10,392,625 B2 | 8/2019 | Jin et al. |
| 10,426,713 B2 | 10/2019 | Song |
| 10,441,519 B2 | 10/2019 | Zhao |
| 10,552,557 B2 | 2/2020 | Frankenbach et al. |
| 10,610,473 B2 | 4/2020 | Hertenstein et al. |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 11,116,703 B2 | 9/2021 | Song et al. |
| 11,116,704 B2 | 9/2021 | Song et al. |
| 11,129,775 B2 | 9/2021 | Song et al. |
| 11,334,694 B2 | 5/2022 | Cetti et al. |
| 11,334,695 B2 | 5/2022 | Cetti et al. |
| 11,904,036 B2 | 2/2024 | Song |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0012646 A1 | 1/2002 | Royce et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0003070 A1 | 1/2003 | Eggers et al. |
| 2003/0008787 A1 | 1/2003 | Mcgee et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180238 A1 | 9/2003 | Sakurai et al. |
| 2003/0180246 A1 | 9/2003 | Frantz et al. |
| 2003/0185867 A1 | 10/2003 | Kerschner et al. |
| 2003/0192922 A1 | 10/2003 | Ceppaluni et al. |
| 2003/0199403 A1 | 10/2003 | Wells |
| 2003/0202952 A1 | 10/2003 | Wells et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0064117 A1 | 4/2004 | Hammons |
| 2004/0131660 A1 | 7/2004 | Lange et al. |
| 2004/0144863 A1 | 7/2004 | Kendrick |
| 2004/0151793 A1 | 8/2004 | Paspaleeva-kuhn et al. |
| 2004/0157754 A1 | 8/2004 | Geary et al. |
| 2004/0229963 A1 | 11/2004 | Stephane Sylvain Culeron |
| 2004/0234484 A1 | 11/2004 | Peffly |
| 2004/0235689 A1 | 11/2004 | Sakai et al. |
| 2005/0003975 A1 | 1/2005 | Browne et al. |
| 2005/0003980 A1 | 1/2005 | Baker |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0192207 A1 | 9/2005 | Morgan, III et al. |
| 2005/0201967 A1 | 9/2005 | Albrecht et al. |
| 2005/0202984 A1 | 9/2005 | Schwartz et al. |
| 2005/0208106 A1 | 9/2005 | Lange et al. |
| 2005/0227902 A1 | 10/2005 | Erazo-majewicz et al. |
| 2005/0233929 A1 | 10/2005 | Queen |
| 2005/0245407 A1 | 11/2005 | Ishihara |
| 2005/0276831 A1 | 12/2005 | Dihora |
| 2006/0002880 A1 | 1/2006 | Peffly |
| 2006/0005333 A1 | 1/2006 | Catalfamo et al. |
| 2006/0009337 A1 | 1/2006 | Smith |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0084589 A1 | 4/2006 | Vlad et al. |
| 2006/0090777 A1 | 5/2006 | Hecht et al. |
| 2006/0094610 A1 | 5/2006 | Yamato et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0166857 A1 | 7/2006 | Surburg et al. |
| 2006/0171911 A1 | 8/2006 | Schwartz et al. |
| 2006/0182703 A1 | 8/2006 | Arisz |
| 2006/0183662 A1 | 8/2006 | Crotty |
| 2006/0210139 A1 | 9/2006 | Carroll |
| 2006/0229227 A1 | 10/2006 | Goldman |
| 2006/0252662 A1 | 11/2006 | Soffin |
| 2006/0263319 A1 | 11/2006 | Fan et al. |
| 2006/0269503 A1 | 11/2006 | Yamazaki |
| 2006/0276357 A1 | 12/2006 | Smith, III et al. |
| 2006/0292104 A1 | 12/2006 | Guskey |
| 2007/0003499 A1 | 1/2007 | Shen et al. |
| 2007/0020263 A1 | 1/2007 | Shitara et al. |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |

(56) References Cited

U.S. PATENT DOCUMENTS

| | | |
|---|---|---|
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0275866 A1 | 11/2007 | Dykstra |
| 2007/0292380 A1 | 12/2007 | Staudigel |
| 2007/0298994 A1 | 12/2007 | Finke et al. |
| 2008/0003245 A1 | 1/2008 | Kroepke et al. |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0176780 A1 | 7/2008 | Warr |
| 2008/0194454 A1 | 8/2008 | Morgan |
| 2008/0206179 A1 | 8/2008 | Peffly et al. |
| 2008/0229512 A1 | 9/2008 | Syed et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0005280 A1 | 1/2009 | Woo et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0240223 A1 | 9/2009 | Warren |
| 2009/0246236 A1 | 10/2009 | Kitko |
| 2009/0312223 A1 | 12/2009 | Yang et al. |
| 2009/0312224 A1 | 12/2009 | Yang et al. |
| 2009/0324505 A1 | 12/2009 | Seidling |
| 2010/0000116 A1 | 1/2010 | Aouad et al. |
| 2010/0001116 A1 | 1/2010 | Johnson |
| 2010/0009285 A1 | 1/2010 | Daems et al. |
| 2010/0061946 A1 | 3/2010 | Scherner et al. |
| 2010/0087357 A1 | 4/2010 | Morgan, III et al. |
| 2010/0152083 A1 | 6/2010 | Velazquez |
| 2010/0168251 A1 | 7/2010 | Warr et al. |
| 2010/0183539 A1 | 7/2010 | Bernhardt |
| 2010/0215775 A1 | 8/2010 | Schmaus et al. |
| 2010/0287710 A1 | 11/2010 | Denutte et al. |
| 2010/0310644 A1 | 12/2010 | Liebmann |
| 2010/0322878 A1 | 12/2010 | Stella et al. |
| 2011/0008267 A1 | 1/2011 | Arkin et al. |
| 2011/0023266 A1 | 2/2011 | Gross et al. |
| 2011/0098209 A1 | 4/2011 | Smets et al. |
| 2011/0107524 A1 | 5/2011 | Chieffi et al. |
| 2011/0118691 A1 | 5/2011 | Nishitani |
| 2011/0139170 A1 | 6/2011 | Hippe et al. |
| 2011/0150815 A1 | 6/2011 | Woo et al. |
| 2011/0165107 A1 | 7/2011 | Derks et al. |
| 2011/0171155 A1 | 7/2011 | Federle |
| 2011/0177017 A1 | 7/2011 | Coffindaffer et al. |
| 2011/0232668 A1 | 9/2011 | Hoffmann et al. |
| 2011/0245126 A1 | 10/2011 | Tsaur et al. |
| 2011/0245134 A1 | 10/2011 | Smets |
| 2011/0245136 A1 | 10/2011 | Smets |
| 2011/0268778 A1 | 11/2011 | Dihora et al. |
| 2011/0269657 A1 | 11/2011 | Dihora et al. |
| 2011/0300095 A1 | 12/2011 | Dente et al. |
| 2011/0303766 A1 | 12/2011 | Smith |
| 2011/0305739 A1 | 12/2011 | Royce |
| 2011/0305778 A1 | 12/2011 | Caggioni et al. |
| 2011/0308555 A1 | 12/2011 | Smets et al. |
| 2011/0308556 A1 | 12/2011 | Smets et al. |
| 2011/0319790 A1 | 12/2011 | Kost et al. |
| 2012/0004328 A1 | 1/2012 | Huchel et al. |
| 2012/0009285 A1 | 1/2012 | Wei et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0052031 A1 | 3/2012 | Troccaz et al. |
| 2012/0100091 A1 | 4/2012 | Hata et al. |
| 2012/0100092 A1 | 4/2012 | Murray |
| 2012/0129924 A1 | 5/2012 | Park et al. |
| 2012/0219610 A1 | 8/2012 | Smith, III et al. |
| 2012/0230936 A1 | 9/2012 | Mikkelsen |
| 2012/0237469 A1 | 9/2012 | Dente et al. |
| 2012/0246851 A1 | 10/2012 | Smith, III et al. |
| 2012/0258150 A1 | 10/2012 | Rauckhorst et al. |
| 2012/0291911 A1 | 11/2012 | Smith |
| 2012/0309660 A1 | 12/2012 | Kawasoe |
| 2012/0316095 A1 | 12/2012 | Wei et al. |
| 2013/0029932 A1 | 1/2013 | Kachi et al. |
| 2013/0034515 A1 | 2/2013 | Stone et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089586 A1 | 4/2013 | Johnson et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0266642 A1 | 10/2013 | Hollingshead et al. |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2013/0319463 A1 | 12/2013 | Policicchio |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0162979 A1 | 6/2014 | Palla-venkata |
| 2014/0171471 A1 | 6/2014 | Krueger |
| 2014/0186864 A1 | 7/2014 | Kato et al. |
| 2014/0201927 A1 | 7/2014 | Bianchetti et al. |
| 2014/0216495 A1 | 8/2014 | Bureiko |
| 2014/0221269 A1 | 8/2014 | Sobel et al. |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2014/0349902 A1 | 11/2014 | Allef et al. |
| 2015/0017152 A1 | 1/2015 | Potechin et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0108163 A1 | 4/2015 | Smith et al. |
| 2015/0110728 A1 | 4/2015 | Jayaswal |
| 2015/0141310 A1 | 5/2015 | Smets et al. |
| 2015/0147286 A1 | 5/2015 | Barrera |
| 2015/0157548 A1 | 6/2015 | De Feij et al. |
| 2015/0218496 A1 | 8/2015 | Schmiedel et al. |
| 2015/0231045 A1 | 8/2015 | Krohn et al. |
| 2015/0262354 A1 | 9/2015 | Periaswamy |
| 2015/0297489 A1 | 10/2015 | Kleinen et al. |
| 2015/0299400 A1 | 10/2015 | Wagner et al. |
| 2015/0313818 A1 | 11/2015 | Stagg |

(56) References Cited

U.S. PATENT DOCUMENTS

| | | |
|---|---|---|
| 2015/0352027 A1 | 12/2015 | Thomas et al. |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0089317 A1 | 3/2016 | Cetti et al. |
| 2016/0089318 A1 | 3/2016 | Cetti et al. |
| 2016/0089322 A1 | 3/2016 | Santos Nogueira et al. |
| 2016/0089462 A1 | 3/2016 | Frankenbach |
| 2016/0089464 A1 | 3/2016 | Frankenbach et al. |
| 2016/0089465 A1 | 3/2016 | Frankenbach et al. |
| 2016/0090555 A1 | 3/2016 | Frankenbach |
| 2016/0090556 A1 | 3/2016 | Frankenbach et al. |
| 2016/0090557 A1 | 3/2016 | Frankenbach et al. |
| 2016/0090558 A1 | 3/2016 | Frankenbach et al. |
| 2016/0092661 A1 | 3/2016 | Hollingshead et al. |
| 2016/0095804 A1 | 4/2016 | Xavier et al. |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0206522 A1 | 7/2016 | Ribaut et al. |
| 2016/0235643 A1 | 8/2016 | Mathonneau et al. |
| 2016/0250115 A1 | 9/2016 | Li et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0296656 A1 | 10/2016 | Scavone et al. |
| 2016/0303043 A1 | 10/2016 | Khoury |
| 2016/0306909 A1 | 10/2016 | Hollingshead et al. |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir et al. |
| 2016/0326458 A1 | 11/2016 | Smets et al. |
| 2016/0338929 A1 | 11/2016 | Zasloff |
| 2016/0354300 A1 | 12/2016 | Thompson et al. |
| 2017/0066579 A1 | 3/2017 | Zillges |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0224607 A1 | 8/2017 | Li et al. |
| 2017/0239155 A1 | 8/2017 | Hartnett |
| 2017/0249407 A1 | 8/2017 | Cetti et al. |
| 2017/0249408 A1 | 8/2017 | Cetti et al. |
| 2017/0252273 A1 | 9/2017 | Renock et al. |
| 2017/0255725 A1 | 9/2017 | Frankenbach et al. |
| 2017/0278249 A1 | 9/2017 | Stofel |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2017/0333591 A9 | 11/2017 | Scavone et al. |
| 2017/0367963 A1 | 12/2017 | Kadir et al. |
| 2018/0004875 A1 | 1/2018 | Cetti et al. |
| 2018/0044097 A1 | 2/2018 | Zeik |
| 2018/0057451 A1 | 3/2018 | Owens et al. |
| 2018/0066210 A1 | 3/2018 | Frankenbach et al. |
| 2018/0098923 A1 | 4/2018 | Hutton, III |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0133133 A1 | 5/2018 | Kleinen et al. |
| 2018/0177708 A1 | 6/2018 | Lee et al. |
| 2018/0221266 A1 | 8/2018 | Zhao et al. |
| 2018/0256481 A1 | 9/2018 | Glenn, Jr. |
| 2018/0280270 A1 | 10/2018 | Rughani et al. |
| 2018/0311135 A1 | 11/2018 | Chang et al. |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2018/0360713 A1 | 12/2018 | Jouy et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran et al. |
| 2019/0105247 A1 | 4/2019 | Song et al. |
| 2019/0117543 A1 | 4/2019 | Zhao |
| 2019/0117544 A1 | 4/2019 | Zhao |
| 2019/0117545 A1 | 4/2019 | Zhao |
| 2019/0125650 A1 | 5/2019 | Lee et al. |
| 2019/0142711 A1 | 5/2019 | Torres Rivera |
| 2019/0142800 A1 | 5/2019 | Ghosh et al. |
| 2019/0155975 A9 | 5/2019 | Cetti et al. |
| 2019/0167554 A1 | 6/2019 | Wankhade |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2019/0328647 A1 | 10/2019 | Chang et al. |
| 2019/0365619 A1 | 12/2019 | Ceballos et al. |
| 2019/0365633 A1 | 12/2019 | Glenn, Jr. |
| 2020/0000690 A1 | 1/2020 | Renock |
| 2020/0078284 A1 | 3/2020 | Botto et al. |
| 2020/0129402 A1 | 4/2020 | Jamadagni |
| 2020/0163846 A1 | 5/2020 | Song |
| 2020/0170894 A1 | 6/2020 | Park et al. |
| 2020/0188243 A1 | 6/2020 | Brown et al. |
| 2020/0197272 A1 | 6/2020 | Hertenstein et al. |
| 2020/0206110 A1 | 7/2020 | Hertenstein et al. |
| 2020/0237628 A1 | 7/2020 | Torres Rivera |
| 2021/0022986 A1 | 1/2021 | Glenn, Jr. |
| 2021/0093543 A1 | 4/2021 | Parikh et al. |
| 2021/0121385 A1 | 4/2021 | Muller et al. |
| 2021/0128444 A1 | 5/2021 | Muller et al. |
| 2021/0128447 A1 | 5/2021 | Galpin et al. |
| 2021/0169765 A1 | 6/2021 | Renock |
| 2021/0212927 A1 | 7/2021 | Hutton, III et al. |
| 2021/0267853 A1 | 9/2021 | Johnson et al. |
| 2021/0275410 A1 | 9/2021 | Hutton, III |
| 2021/0353518 A1 | 11/2021 | Ballhaus et al. |
| 2021/0353522 A1 | 11/2021 | Ballhaus et al. |
| 2021/0401716 A1 | 12/2021 | Gogineni et al. |
| 2022/0062136 A1 | 3/2022 | Feng |
| 2022/0175640 A1 | 6/2022 | Herteinstein et al. |
| 2022/0323337 A1 | 10/2022 | Yamazaki |

(56) References Cited

U.S. PATENT DOCUMENTS

| | | | |
|---|---|---|---|
| 2022/0378680 A1 | 12/2022 | Ballhaus et al. | |
| 2022/0378684 A1 | 12/2022 | Cochran et al. | |
| 2022/0395444 A1 | 12/2022 | Hutton, III | |

FOREIGN PATENT DOCUMENTS

| | | |
|---|---|---|
| CA | 704195 A | 2/1965 |
| CA | 1248458 A | 1/1989 |
| CA | 2078375 A1 | 3/1994 |
| CN | 1263455 A | 8/2000 |
| CN | 1286612 A | 3/2001 |
| CN | 1545404 A | 11/2004 |
| CN | 1823929 A | 8/2006 |
| CN | 100534415 C | 9/2009 |
| CN | 101112349 B | 5/2011 |
| CN | 101690697 B | 10/2011 |
| CN | 101559034 B | 1/2013 |
| CN | 102895151 A | 1/2013 |
| CN | 102973437 A | 3/2013 |
| CN | 102697668 B | 8/2013 |
| CN | 103356408 A | 10/2013 |
| CN | 102697670 B | 7/2014 |
| CN | 104107401 A | 10/2014 |
| CN | 102851015 B | 12/2014 |
| CN | 105726393 A | 7/2016 |
| CN | 105769617 A | 7/2016 |
| CN | 106659664 A | 5/2017 |
| CN | 106750361 A | 5/2017 |
| CN | 107595657 A | 1/2018 |
| CN | 107595673 A | 1/2018 |
| CN | 107648096 A | 2/2018 |
| CN | 107737329 A | 2/2018 |
| CN | 107961212 A | 4/2018 |
| CN | 108186385 A | 6/2018 |
| CN | 108283583 A | 7/2018 |
| CN | 108451858 A | 8/2018 |
| CN | 110279591 A | 9/2019 |
| CN | 110960434 A | 4/2020 |
| DE | 2145204 A1 | 3/1973 |
| DE | 3018456 A1 | 11/1981 |
| DE | 4315396 A1 | 11/1994 |
| DE | 102004012009 A1 | 9/2005 |
| DE | 202005009618 U1 | 9/2005 |
| DE | 102004023720 A1 | 12/2005 |
| DE | 102014225083 A1 | 10/2015 |
| DE | 102014225606 A1 | 10/2015 |
| DE | 102015204987 A1 | 9/2016 |
| EP | 0108517 A2 | 5/1984 |
| EP | 0574086 A2 | 12/1993 |
| EP | 0666358 A1 | 8/1995 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 1842572 A2 | 10/2007 |
| EP | 2005939 A1 | 12/2008 |
| EP | 1970045 A3 | 9/2009 |
| EP | 2042216 B1 | 9/2015 |
| EP | 3121210 A1 | 1/2017 |
| EP | 3260171 A1 | 12/2017 |
| EP | 3622946 A1 | 3/2020 |
| ES | 2052450 B1 | 12/1994 |
| FR | 2669531 A1 | 5/1992 |
| FR | 2795955 A1 | 1/2001 |
| GB | 190110699 A | 8/1901 |
| GB | 191023922 A | 10/1911 |
| GB | 1347950 A | 2/1974 |
| GB | 2048229 | 12/1980 |
| GB | 2450727 A | 1/2009 |
| HU | 42318 | 8/1986 |
| JP | S56011009 A | 12/1981 |
| JP | S58113300 A | 7/1983 |
| JP | S58198412 A | 11/1983 |
| JP | AS60004598 A | 1/1985 |
| JP | S61236708 A | 10/1986 |
| JP | S62205200 A | 9/1987 |
| JP | S63501221 A | 5/1988 |
| JP | S63165308 A | 7/1988 |
| JP | H04364114 A | 12/1992 |
| JP | H06220495 A | 8/1994 |
| JP | H0753340 A | 2/1995 |
| JP | 07252134 | 10/1995 |
| JP | H08310924 A | 11/1996 |
| JP | 09020618 A | 1/1997 |
| JP | 09030938 A | 2/1997 |
| JP | H09175961 A | 7/1997 |
| JP | H10017894 A | 1/1998 |
| JP | H11139944 A | 5/1999 |
| JP | 2964226 B2 | 10/1999 |
| JP | 2000178586 A | 6/2000 |
| JP | 3069802 B2 | 7/2000 |
| JP | 2001011492 A | 1/2001 |
| JP | 2001011497 A | 1/2001 |
| JP | 2001254099 A | 9/2001 |
| JP | 2001261529 A | 9/2001 |
| JP | 2003201217 A | 12/2001 |
| JP | 2002179552 A | 6/2002 |
| JP | 2002226889 A | 8/2002 |
| JP | 2002285191 A | 10/2002 |
| JP | 2002336337 A | 11/2002 |
| JP | 2003055699 A | 2/2003 |
| JP | 2003082398 A | 3/2003 |
| JP | 2003171688 A | 6/2003 |
| JP | 2003176497 A | 6/2003 |
| JP | 2003261413 A | 9/2003 |
| JP | 2003268398 A | 9/2003 |
| JP | 3480165 B2 | 12/2003 |
| JP | 2003342131 A | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006063044 A | 3/2006 |
| JP | 2006104149 A | 4/2006 |
| JP | 2006124312 A | 5/2006 |
| JP | 2006183039 A | 7/2006 |
| JP | 2006193549 A | 7/2006 |
| JP | 2006249092 A | 9/2006 |
| JP | 2006282565 A | 10/2006 |
| JP | 2007131687 A | 5/2007 |
| JP | 2007177047 A | 7/2007 |
| JP | 2007223935 A | 9/2007 |
| JP | 2008001626 A | 1/2008 |
| JP | 2008214292 A | 9/2008 |
| JP | 2009096778 A | 5/2009 |
| JP | 2009120559 A | 6/2009 |
| JP | 2009161866 A | 7/2009 |
| JP | 2011153167 A | 8/2011 |
| JP | 2011190221 A | 9/2011 |
| JP | 2011241353 A | 12/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 2013155143 A | 8/2013 |
| JP | 2013193968 A | 9/2013 |
| JP | 2013216639 A | 10/2013 |
| JP | 6046394 B2 | 1/2014 |
| JP | 2014009177 A | 1/2014 |
| JP | 2014024875 A | 2/2014 |
| JP | 2014037383 A | 2/2014 |
| JP | 2014091723 A | 5/2014 |
| JP | 2014234350 A | 12/2014 |
| JP | 5667790 B2 | 2/2015 |
| JP | 2015034157 A | 2/2015 |
| JP | 2015101545 A | 6/2015 |
| JP | 2015129099 A | 7/2015 |
| JP | 2016013973 A | 1/2016 |
| JP | 2016030722 A | 3/2016 |
| JP | 2016088910 A | 5/2016 |
| JP | 6184550 B1 | 8/2017 |
| JP | 2018012673 A | 1/2018 |

(56) References Cited

FOREIGN PATENT DOCUMENTS

| | | |
|---|---|---|
| KR | 100290589 B1 | 9/2001 |
| KR | 100821846 B1 | 4/2008 |
| KR | 1020080111280 A | 12/2008 |
| KR | 20090095359 A | 9/2009 |
| KR | 20100040180 A | 4/2010 |
| KR | 20140060882 A | 5/2014 |
| KR | 101494008 B1 | 2/2015 |
| KR | 101503922 B1 | 3/2015 |
| KR | 101532070 B1 | 7/2015 |
| UA | 50333 U | 5/2010 |
| WO | 8603679 A1 | 7/1986 |
| WO | 9114759 A1 | 10/1991 |
| WO | 91017237 A1 | 11/1991 |
| WO | 9213520 A1 | 8/1992 |
| WO | 199325650 A1 | 12/1993 |
| WO | 9417783 A2 | 8/1994 |
| WO | 9502389 A2 | 1/1995 |
| WO | 9726854 A1 | 7/1997 |
| WO | 9823258 A1 | 6/1998 |
| WO | 9906010 A2 | 2/1999 |
| WO | 9918928 A1 | 4/1999 |
| WO | 9924004 A1 | 5/1999 |
| WO | 9924013 A1 | 5/1999 |
| WO | 9949837 A1 | 10/1999 |
| WO | 9957233 A1 | 11/1999 |
| WO | 0012553 A1 | 3/2000 |
| WO | 0032601 | 6/2000 |
| WO | 0119949 A1 | 3/2001 |
| WO | 0142409 A1 | 6/2001 |
| WO | 0148021 A1 | 7/2001 |
| WO | 2001076552 A2 | 10/2001 |
| WO | 2003051319 A1 | 6/2003 |
| WO | 03096998 A1 | 11/2003 |
| WO | 2004078901 A1 | 9/2004 |
| WO | 2005023975 A1 | 3/2005 |
| WO | 2008017540 A1 | 2/2008 |
| WO | 2008128826 A1 | 10/2008 |
| WO | 2008145582 A1 | 12/2008 |
| WO | 2009016555 A2 | 2/2009 |
| WO | 2009030594 A1 | 3/2009 |
| WO | 2009053931 A2 | 4/2009 |
| WO | 2010026009 A1 | 3/2010 |
| WO | 2010052147 A2 | 5/2010 |
| WO | 2011124560 A2 | 10/2011 |
| WO | 2012017091 A2 | 2/2012 |
| WO | 2012052536 A2 | 4/2012 |
| WO | 2012055587 A1 | 5/2012 |
| WO | 2012055812 A1 | 5/2012 |
| WO | 2012084970 A1 | 6/2012 |
| WO | 2012127009 A1 | 9/2012 |
| WO | 2012136651 A1 | 10/2012 |
| WO | 2013010706 A2 | 1/2013 |
| WO | 2013018805 A1 | 2/2013 |
| WO | 2013119908 A1 | 8/2013 |
| WO | 2014073245 A1 | 5/2014 |
| WO | 2014073456 A1 | 5/2014 |
| WO | 2014111667 A2 | 7/2014 |
| WO | 2014111668 A2 | 7/2014 |
| WO | 2014148245 A1 | 9/2014 |
| WO | 2015016037 A1 | 2/2015 |
| WO | 2015067779 A1 | 5/2015 |
| WO | 2015085376 A1 | 6/2015 |
| WO | 2015122371 A1 | 8/2015 |
| WO | 2015141787 A1 | 9/2015 |
| WO | 2016049389 A1 | 3/2016 |
| WO | 2016147196 A1 | 9/2016 |
| WO | 2017052161 A1 | 3/2017 |
| WO | 2017140798 A1 | 8/2017 |
| WO | 2017140802 A1 | 8/2017 |
| WO | 2017207685 A1 | 12/2017 |
| WO | 2018023180 A1 | 2/2018 |
| WO | 2018064511 A1 | 4/2018 |
| WO | 2018109148 A1 | 6/2018 |
| WO | 2019030458 A2 | 2/2019 |
| WO | 2019074990 A1 | 4/2019 |
| WO | 2019074992 A1 | 4/2019 |
| WO | 2019200027 A1 | 10/2019 |
| WO | 2020005309 A1 | 1/2020 |
| WO | 2020030732 A1 | 2/2020 |
| WO | 2021026572 A1 | 2/2021 |
| WO | 2021099088 A1 | 5/2021 |
| WO | 2021127318 A1 | 6/2021 |
| WO | 2021144326 A1 | 7/2021 |
| WO | 2021231510 A1 | 11/2021 |

OTHER PUBLICATIONS

Anonymous: "Anti-Dandruff Scalp Care Shampoo", Mintel, Database accession No. 301924, Sep. 16, 2004, 2 pages.
All Office Actions; U.S. Appl. No. 17/874,589, filed Jul. 27, 2022.
Unpublished U.S. Appl. No. 17/874,589, filed Jul. 27, 2022, to Sean Michael Renockr et. al.
"Anti-Dandruff Shampoo", Mintel Database, Record No. 752198, dated Aug. 2007 ; pp. 1-3.
"Dandruff Control Shampoo", Mintel Database, Record No. 2300131, dated Jan. 2014; pp. 1-2.
"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.
"Natural Detangling Shampoo", Mintel Database, dated Sep. 13, 2017; 2 pages.
"Soda Shampoo", Mintel Database, dated Apr. 2015; pp. 1-4.
"Treatment Foam for Recurrent Scaling Conditions", Mintel Database, Aug. 2007; pp. 1-2.
Air Quality of the Iowa Department of Natural Resources. A Review of the Science and Technology of Odor Measurement, 2005, 51 pages (2005).
Anonymous: "Merquat Polyquaternium 47 Series, Water Soluble Polymers for Personal Care", Jul. 30, 2017, URL: https://www.in-cosmetics.com/_novadocuments/2729, retrieved on Dec. 21, 2018 ; 1 page.
Anonymous: "Naturally Derived Body Wash", Database GNPD [Online] Mintel; Feb. 15, 2021, 2 pages.
Anonymous: "Peptide Shampoo", Database GNPD [Online] Mintel; Dec. 14, 2015, 3 pages.
Anonymous: "Replenishing Moisture Shampoo", Database GNPD [Online] Mintel, Mar. 10, 2015br.
Anonymous: "Shampoo", Database GNPD [Online] Mintel, Jan. 26, 2021, 3 pages.
Anonymous: "Shampooing au Phytolait d'abricot—Formule N° 102-MP06-MI3-AA03",Internet Citation, Feb. 19, 2005, Retrieved from the Internet:URL: http://web.archive.org/web/20050219040350/www.albanmuller.com/francais/catalogue/formules/formul10.asp, 1 page.
ASTM D3954-94, Reapproved 2010, vol. 15.04, Standard Test Method for Dropping Point of Waxes.
BASF, "Practical Guide to Rheology Modifiers", download from https://insights.basf.com/flles/BASF_ED_RheologyModifiers_download.pdf on Nov. 1, 2022. (Year: 2022).
Brattoli et al. Odour Detection Methods: Offactometry and Chemical Sensors. Sensors (Basel), 2011; 11(5); 5290-5322 (2011).
Carbopol Aqua SF-1 Polymer Technical Data Sheet, TDS-294, dated Dec. 2000 ; pp. 1-9.
Chemical Book (Chemical Book, Isolongifolone, available at http://www.chemicalbook.com/ProductChemicalPropertiesCB5318980_EN.htm), no date available.
Christensen et al., "Experimental Determination of Bubble Size Distribution in a Water Column by Interferometric Particle Imaging and Telecentric Direct Image Method", Student Report, Aalborg University; dated Jun. 3, 2014; 123 pages.
Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.
D'Souza et al., Shampoo and Conditioners: What a Dermatologist Should Know? Indian J Dermatol, dated May-Jun. 2015; pp. 60(3), 248-254 (2015).

(56) References Cited

OTHER PUBLICATIONS

Database GNPD [Online] Mintel;Mar. 28, 2018 (Mar. 28, 2018),anonymous: Dandruff Control Shampoo 11,XP055787038, Database accession No. 5556267abstract.
Database GNPD [Online] Mintel;Apr. 5, 2005 (Apr. 5, 2005),anonymous: "Anticaspa-Graso Anti-DandruffShampoo",XPC:I55787029,Database accession No. 351776paragraph [ingredients].
Database GNPD [Online] Mintel; Jan. 6, 2020 (Jan. 6, 2020),anonymous: 11 Shampoo 11, 3 pages.
Database WPI; Week 201459; Thomson scientific, London, GB; AN 2014-P66521; XP002752638.
Datasheet: Empigen Total Active TC/U, Datasheet, dated Jan. 31, 2017 (Innospec) ; 2 pages.
Dehyquart Guar: Published dated Nov. 2010 ; pp. 1-34.
Fevola, Michael J. "Guar Hydroxypropyltrimonium Chloride." Cosmetics and toiletries; vol. 127.1; Jan. 2012 ; pp. 16-21.
Grillet et al., "Polymer Gel Rheology and Adhesion", Rheology, 2012, pp. 59-80.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet:URL:https://www.happi.com/contents/view_formulary/2009-10-01/sulfate-free-surfactants-conditioning-shampoo/, XP002804301, Jan. 10, 2019, 1 page.
Inspection certificate for Hostapon® CCG, Clariant Ibérica Production, S.A., May 6, 2019; p. 1-2.
McGinley et al. American Association of Textile Chemists and Colorists, 2017, 17 pages, (2017).
McGinley et al. Performance Verification of Air Freshener Products and Other Odour Control Devices for Indoor Air Quality Malodours. Presented at the 8th Workshop on Odour and Emissions of Plastic Materials Universitat Kassel Institut for Wesrkstofftechnik Kassel, Germany, Mar. 27-28, 2006, 13 pages.
Medvedev, Diffusion Coefficients in Multicomponent Mixtures, PhD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Morioka, H. et al. "Effects of Zinc on the New Preparation Method of Hydroxy Double Salts" Inorg. Chem. 1999, 38, 4211-6.
Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Noritomi H. Formation and Solubilization Property of Water-in-Oil Microemulsions of Alkyl Glucoisdes. Advances in Nanoparticles, 2013, 2, 366-371 (Year: 2013).
Parchem fine & specialty chemicals. MIPA—laureth sulfate supplier distributor—CAS 83016-76-6; dated 2021; pp. 1-7.
Perm Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-theSafety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Sheet for Chemoryl™ LS Surfactant, Sodium Lauroyl Sarcosinate, Lubrizol Advanced Materials, Inc., Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
Rajendran A. et al: "Study on the Analysis of Trace Elements in Aloe veraand Its Biological Importance Study on the Analysis of Trace Elements in Aloe vera and Its Biological Importance", Journal of Applied Sciences Research, Jan. 1, 2007 (Jan. 1, 2007), XP055799133, pp. 1476-1478.
Robinson et al., Final Report of the Amended Safety Assessment of Sodium Laureth Sulfate and Related Salts of SulfatedEthoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics , dated Sep. 20, 2013, 46 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Sensory.,"A Review of the Science and Technology of Odor Measurement", Prepared for the Air Quality Bureau of the Iowa Department of Natural Resources, Dec. 30, 2005 51 pages.
Softazoline CL-R, Kawaken Singapore PTE Ltd. Website printout from http://kawaken.com.sg/softazoline-ch-r//a, accessed on Nov. 30, 2022.
Todd et al., Volatile Silicone Fluids for Cosmetics, Cosmetics and Toiletries, vol. 91, pp. 27-32 (Jan. 1976).
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates andGuidelines of Corona Virus View project health and beauty science View project Rohit Bhavsar Reliance Industries Limited; International Journal for Research inApplied Science & Engineering Technology, Apr. 1, 2020 (Apr. 1, 2020)t XP055842327, DOI: 10.22214, 14 pages.
"Deep Image Matting", Ning Xu et al, Beckman Institute for Advanced Science and Technology, University of Illinois at Urbana-Champaign, Adobe Research, dated Mar. 10, 2017; 10 pages.
Shampoo, ID# 6148479, Mintel GNPD [online], URL: http://www.gnpd.com, Nov. 2018, 4 pages.
"Personal care solutions Guide", Solvay, Publication date: May 2018, 84 pages.
Product Data Record Tego® Betain F KB 5, dated Jul. 1, 2015, 4 pages.
Anonymous, "Healing + Anti-Breakage Shampoo", ID# 3383875, Mintel GNPD, URL: http://www.gnpd.com, dated Aug. 2015, 3 pages.
Anonymous, "Shampoo", ID# 1743027, Mintel GNPD, URL: http://www.gnpd.com, dated Mar. 2012, 3 pages.
Technical Information: TEGO® Betain F KB 5 / TEGO® Betain F KM 1; Mild amphoteric surfactants: www.evonik.com/personal-care; Jul. 2010; 2 pages; Product Specification; 5 pages.
"Jaguar® Optima", Solvay, site: www.solvay.com, year 2023, 1 page.
Cafasso, "What's the proper order to use shampoo and conditioner while bathing", Healthline, Retrieved from Internet: https://www.healthline.com/health/beauty-skin-care/shampoo-or-conditioner-first, dated Jul. 13, 2020, 2 pages.

(56) References Cited

OTHER PUBLICATIONS

Duis et al., "Environmental fate and effects of water-soluble synthetic organic polymers used in cosmetic products", Enviromental Sciences Europe, 33:21, Year 2021; 20 pages.

Matsouka et al., "Vesicle formation of disodium lauryl sulfosuccinate", Journal of Molecular Liquids, 348, 118422, Nov. 1, 2021, 7 pages.

Ramachandra et al, "Processing of Aloe Vera Leaf Gel: A Review", American Journal of Agricultural and Biological Sciences 3 (2), year 2008, pp. 502-510.

Yang et al., "Synthesis and foaming performance of Lauramidopropyl Betaine Derivate Surfactants", Materials Science Forum, vol. 953, Jan. 9, 2019, 1 page.

Anonymous, "Medicated Cleanser", Nioxin Research Laboratories, Mintel GNPD [online], ID:1060983, URL: http://www.gnpd.com, dated Feb. 2009, 4 pages.

P. A. Cornwell, "A review of shampoo surfactant technology: consumer benefits, raw materials and recent developments", International Journal of Cosmetic Science, 40 , Oct. 27, 2017, pp. 16-30.

Sbhatu et al, "Formulation and Physicochemical Evaluation of Lab-Based Aloe adigratana Reynolds Shampoos", Hindawi, International Journal of Analytical Chemistry, vol. 2020, Article ID 6290617, URL: https://www.ncbi.nlm.nih.gov/pmc/articles/PMC7160718/, Published Apr. 4, 2020, 7 pages.

Shampoo Manufacturing Plant, Lodha International, URL: https://www.lodhapharma.com/shampoo-manufacturing-plant.php#:~:text=Shampoos%20are%20categorized%20as%20viscous,if%20not%20all%20of%20them, Published: 2018, 4 pages.

Anonymous: "Acne Foaming Cleanser", Database GNPD [Online] Mintel, XP055591421, Jul. 29, 2016, 03 Pages.

Anonymous: "Naturally Rich Moisturizing Shampoo", Database GNPD [Online] Mintel, XP55897729, Mar. 27, 2019, 03 Pages.

Anonymous: "Shampoo C", Database GNPD [Online] Mintel, Sep. 29, 2011, 03 Pages.

Cross-polarized light microscopy image:

The cross-polarized image captured represents Maltese crosses which are typical for lamellar droplets

FIG. 3
Cryo SEM

FIG. 4
Cryo TEM: Samples representative of structures formed

PERSONAL CARE COMPOSITION

FIELD OF THE INVENTION

The present disclosure generally relates to personal care compositions free of sulfonated surfactants which gently clean and deliver anti-dandruff actives to the scalp.

BACKGROUND OF THE INVENTION

Human hair becomes soiled due to contact with the surrounding environment and from sebum secreted by the scalp. Soiled hair has a dirty feel and exhibits an unattractive appearance. Application and washing of the soiled hair with a shampoo composition can restore hair to a clean and attractive appearance by removing oil and other soils from the hair. Known shampoo compositions typically remove oil and soil from hair through inclusion of sulfated surfactants. Shampoos including sulfated surfactants, such as sodium lauryl sulfate and sodium laureth sulfate, however, can exhibit a number of undesirable characteristics such as poor-quality hair feel as well as hair and skin dryness after washing. Shampoos including sulfated surfactants also face poor consumer acceptance as a consequence of this perceived harshness. Consequently, it would be desirable to provide personal care compositions which can provide acceptable cleaning quality to soiled hair, while additionally delivering consumer desired anti-dandruff benefits. The product may additionally be substantially free of silicones.

SUMMARY OF THE INVENTION

A personal care composition that includes sodium cocoyl alaninate; a glyceryl ester; an antidandruff agent; a liquid carrier; and is substantially free of sulfated surfactants. In some aspects, the personal care composition includes sodium cocoyl alaninate; a glyceryl ester; an antidandruff agent; a liquid carrier; is substantially free of sulfated surfactants; and comprises unilamellar, multilamellar, or oligovesicular vesicles.

DETAILED DESCRIPTION OF THE INVENTION

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

With regard to the compositions described herein, all percentages are by weight of the composition, unless specifically stated otherwise. All ratios are weight ratios, unless specifically stated otherwise. All such weights as they pertain to listed ingredients are based on the active level and do not include carriers or by-products that may be included in commercially available materials, unless otherwise specified. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

"About" modifies a particular value by referring to a range equal to plus or minus twenty percent (+/−20%) or less (e.g., less than 15%, 10%, or even less than 5%) of the stated value.

"Charge density" refers to the ratio of the number of positive charges on a polymer to the molecular weight of said polymer.

"Derivative" means an amide, ether, ester, amino, carboxyl, acetyl, and/or alcohol derivatives of a given compound.

"Hair care" means regulating and/or improving a hair and/or scalp condition such as, for example, improving hair appearance (e.g., volume, bounce, shine, texture) and improving hair and/or scalp health (e.g., dandruff, breakage, split-ends, fall-out).

"Hair care active" means a compound or combination of compounds that, when applied to the hair or scalp, provide an acute and/or chronic benefit to the hair and/or scalp or a type of cell commonly found therein.

"Hair care composition" means a composition that includes a hair care active and regulates and/or improves a hair and/or scalp condition.

"Personal care composition" means a composition intended to be topically applied to hair and/or skin. Personal care compositions may be in the form of a solution, dispersion, emulsion, powder, talc, capsules, sphere, sponge, solid dosage forms, foams, combinations of these and the like. Some non-limiting examples of personal care compositions include hair tonics, leave-on hair products such as treatment, and styling products, rinse-off hair products such as shampoos, conditioners, body washes, and soaps.

The term "polymer," as used herein, includes materials whether made by polymerization of one type of monomer or made by two (i.e., copolymers) or more types of monomers.

The term "suitable for application to human hair," as used herein, means that the personal care compositions or components thereof, are acceptable for use in contact with human hair and the scalp and skin without undue toxicity, incompatibility, instability, allergic response, and the like.

"Substantially free" refers to a composition that contains less than 3% (e.g., less than 2%, 1%, 0.5%, 0.25%, 0.1%, 0.01% or even 0%) of a subject ingredient. For example, a composition that is "substantially free of sulfates" may refer to a composition that only includes sulfate-containing compounds incidentally incorporated as minor components (e.g., carryover ingredients) at a level of less than 0.1%.

"Sulfate free" means the composition is contains no detectable sulfated surfactants (i.e., 0%).

"Sulfated surfactants" means surfactants that contain a sulfate group.

The term "water soluble," as used herein, means that the material is soluble in water. In certain embodiments, the material can be soluble at 25° C. at a concentration of 0.1% by weight of the water solvent, in certain embodiments at 1% by weight of the water solvent, in certain embodiments at 5% by weight of the water solvent, and in certain embodiments at 15% or more by weight of the water solvent.

Personal Care Compositions

As will be described herein, a personal care composition is disclosed which exhibits excellent cleaning qualities without the use, or inclusion, of a sulfated surfactant; while also delivering an anti-dandruff benefit. The personal care compositions herein contain sodium cocoyl alaninate; a glyceryl ester; an antidandruff agent; and a liquid carrier. The personal care compositions described herein are substantially free of sulfated surfactants and, ideally, are sulfate free. Additionally, the personal care composition may be substantially free of silicones, such as polydimethylsiloxanes. Further, the personal care composition may comprise less than 6% added salts, (e.g., less than 3%, 2% or even 0%). In some aspects, the sodium cocoyl alaninate and the glyceryl ester are included at a weight ratio of 5:1 to 1:2 (e.g., 9:2 to 1:1, 4:1 to 2:1, or 3:1 to 3:2). The viscosity of the personal care composition can be 1 mPa-s to 12 Pa-s (e.g., 3 mPa-s to 10 Pa-s, 10 mPa-s to 5 Pa-s, or even 100 mPa-s to 3 Pa-s).

Personal care compositions such as sulfate free micellular-type shampoos have historically been difficult to thicken, stabilize, and deposit particulate actives, such as antidandruff actives, without polymeric thickeners or suspending agents such as polyacrylic acids (e.g., carbomers), ethylene glycol distearate (EGDS) or trihydroxystearin (e.g., THIXCIN from Elementis, New Jersey). It has been found that personal care compositions that deliver antidandruff benefits and are sulfate free can be thickened, stabilized, and deposit both soluble and insoluble antidandruff actives equal to or greater than sulfate containing antidandruff personal care compositions. This can be accomplished via the formation of lamellar vesicles when a sulfate free amino based surfactant such as sodium cocoyl alaninate combines with a glyceryl ester in the presence of a cationic polymer. It has been further found that soluble antidandruff actives such as, for example, piroctone olamine can be incorporated into the lamellar vesicles and deposited efficiently via coacervate formation generated via anionic surfactant and cationic polymer to the human scalp. These products also provide a benefit for insoluble antidandruff actives like zinc pyrithione. These insoluble actives can be stabilized via the vesicles which generate a high, low-shear yield stress relative to a micellular system, which typically requires EGDS or a polymeric thickener for suspension and stability. Coacervate aided delivery of hair care actives in this system is efficient and can effectively deposit an insoluble antidandruff active on the hair and/or scalp.

The personal care compositions herein have a low-shear yield stress value of 0.005 Pa to 20 Pa (e.g., 0.01 to about 10 Pa or 0.1 to 6 Pa). This low-shear yield stress value enables the stable inclusion of particulate actives. Further, the personal care composition can be stable at 5° C. and/or 40° C. Low-shear yield stress can be determined according to the Rheology method described in more detail below.

Figure 1:
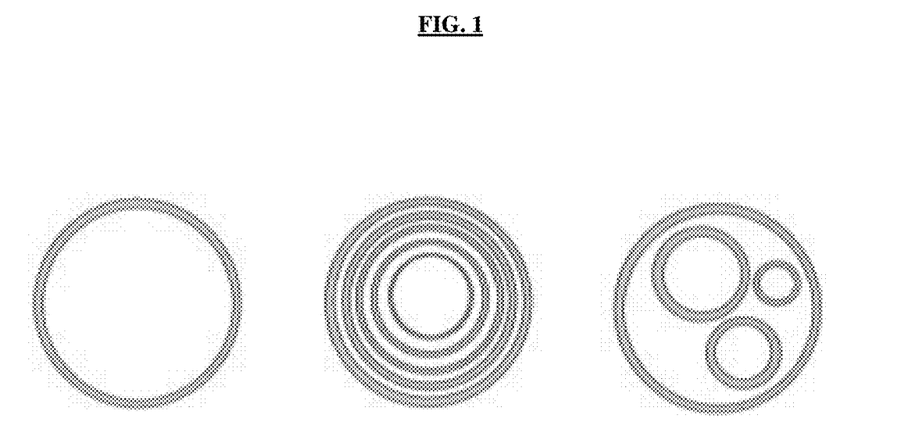
FIG. 1 shows vesicles. Figure on the left is representative of unilamellar, Figure in the middle is representative of multilamellar. Figure on the right representative of oligovesicular.
Figure 2:
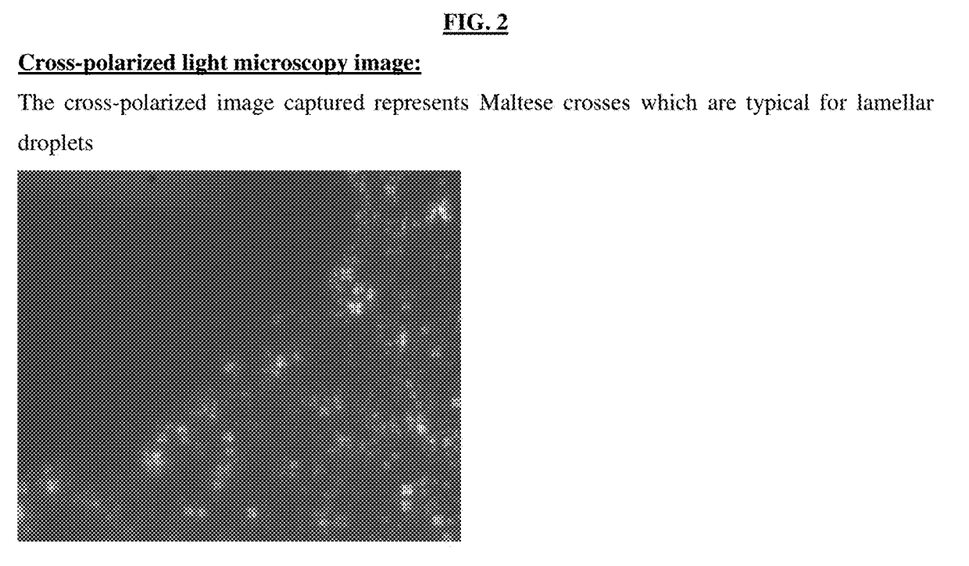
FIG. 2 is a Cross-polarized light microscopy image. The cross-polarized image captured represents Maltese crosses which are typical for lamellar droplets
Figure 3:
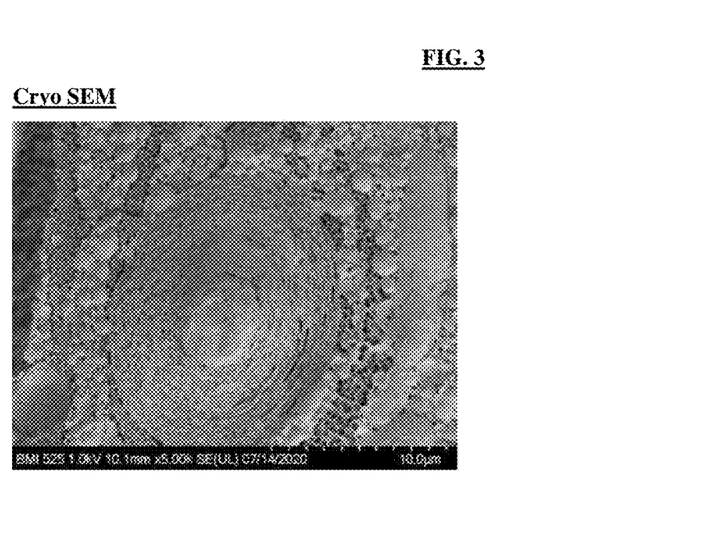
FIG. 3 is a Cryo SEM showing a freeze fractured cross section of a multilamellar vesicle.
Figure 4:
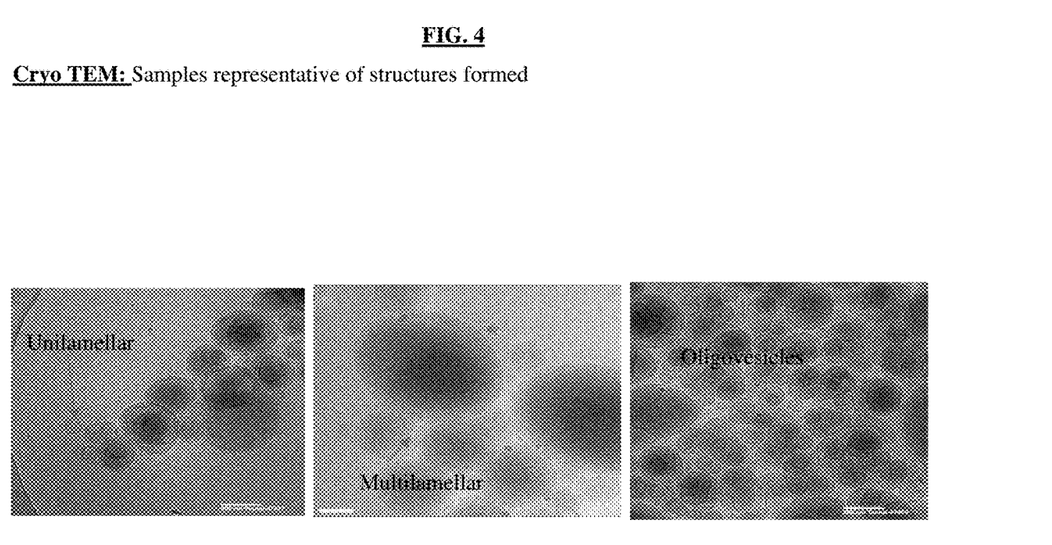
FIG. 4 is a Cryo TEM: samples representative of vesicle structures formed.

Vesicles typically form upon pH adjustment of the composition. Vesicle formation helps structure the formulation and will typically cause the composition to transition from transparent or translucent to opaque (e.g., from clear to white). The vesicles can be unilamellar, multilamellar or oligovesicles. A unilamellar vesicle is a spherical chamber, bounded by a single bilayer of an amphiphilic lipid or a mixture of such lipids, containing aqueous solution inside the chamber. A multilamellar vesicle contains multiple spherical chambers, bound by multiple bilayers of an amphiphilic lipid or a mixture of such lipids, containing aqueous solution inside the chamber. Oligovesicular vesicles are spherical chambers bound by a single bilayer of amphiphilic lip or a mix of such lipids which contains aqueous solution inside the chamber in addition to other independent spherical vesicles within the main vesicle. The presence of vesicles can be seen using cross-polarized light microscopy, SEM, and cryo SEM and cryo TEM, as is well known in the art. Examples of vesicles are illustrated in FIGS. 1-3. FIG. 1 shows the structure of unilamellar (left), multilamellar (center), and oligovesicles (right).

It may be consumer desirable to have a personal care composition, such as a shampoo, with a minimal level of ingredients. The personal care compositions herein allow for a minimized amount of ingredients without polymeric thickeners or suspending agents such as carbomers, EGDS or trihydroxystearin, etc. A personal care composition in the form of a shampoo as described herein may consist of some or all of the following ingredients: water, sodium cocoyl alaninate, glyceryl caprylate/caprate, cationic polymer, sodium benzoate, citric acid, perfume, antidandruff active; and sodium chloride. It is understood that perfumes can be formed from one or more fragrances.

Detersive Surfactant

The personal care compositions described herein include sodium cocoyl alaninate, which is a detersive surfactant. Detersive surfactants such as sodium cocoyl alaninate generally provide a cleaning benefit to soiled hair and hair follicles by facilitating the removal of oil and other soil components from the soiled hair. The surfactant facilitates such cleaning due to its amphiphilic nature which allows micelles to form around oil and other soils in the hair which can then be rinsed from the hair. Sodium cocoyl alaninate is an anionic amino acid (alanine) and coconut fatty acid-derived surfactant. This surfactant is sulfate free, biodegradable, hypoallergenic, and mild to the skin and eyes. Sodium cocoyl alaninate delivers mild cleansing, which imparts pleasant moisturizing feel after drying. The sodium cocoyl alaninate may be present at 5% to 20% (e.g., 6%-15%, 7%-12%, or 8%-10%). Sodium cocoyl alaninate can be sourced from Ajinomoto and Sino Lion.

Glyceryl Ester

In some aspects, the personal care composition contains 1% to 20% (e.g., 2.5% to 15%, 3% to 12%, 4% to 10%, or 5% to 8%) glyceryl ester. Some non-limiting examples of glyceryl esters are glyceryl caprylate, glyceryl caprate, and polyglyeryl esters such as polyglyceryl 2-triisostearate. Other glyceryl esters can be selected from compounds containing C8-C10 mono-, di- and triglycerides which are different from C8-C10 mono- or dicaprylate 1,2,3-propanetriol. A mixture of glyceryl caprylate and glyceryl caprate (e.g., sourced from Stepan) may be particularly suitable for use in the present composition because it is mild and substantially free of polyethylene glycol, ethylene oxide/propylene oxide, and nitrogen. The multifunctional benefits of glyceryl caprylate/caprate include yield generation for suspension of particles at high temperature for product stability, viscosity modifier, enhanced preservation activity, scalp skin moisturization, wet and dry conditioning, and potential enhanced deposition of soluble active. Further examples of glyceryl esters that may be suitable for use herein can be found in U.S. Pat. No. 10,265,261.

In some aspects, the personal care composition may include 1% to 20% (e.g., 2.5% to 15% or 3% to 10%) glyceryl ester in combination with lauric acid. The lauric acid may be present in the composition at 0.1% to 3%, (e.g., 0.1% to 2.5%).

The composition may include a zwitterionic co-surfactant, wherein the zwitterionic surfactant is a derivative of an aliphatic quaternary ammonium, phosphonium, or sulfonium compound, in which the aliphatic radicals can be straight or branched chain, and wherein one of the aliphatic substituents contains 8 to 18 carbon atoms and one contains an anionic group such as carboxy, sulfonate, sulfate, phosphate or phosphonate. Some non-limiting examples of zwitterionic surfactants are: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, cocosultaine, lauramidopropyl betaine, lauryl betaine, lauryl hydroxysultaine, lauryl sultaine, and mixtures thereof. A suitable zwitterionic surfactant is lauryl hydroxysultaine.

Cationic Polymers

The personal care composition here may include a cationic deposition polymer. The cationic deposition polymer can be present at 0.1% to 3% (e.g., 0.1% to 2.0% or 0.1% to 1.0%). The cationic polymer can be guar, cellulose, a derivative of these or a combination thereof. The cationic deposition polymer can have a weight average molecular weight of 500,000 daltons (da) to 2.2 Mda (e.g., 800 Kda to about 2 Mda); and a charge density of from 0.4 meq/g to 2.6 meq/g (e.g., 0.4 to 2, 0.7 to 2, or 0.6 to 1.6). Methods of determining charge density well-known and can be determined at the pH of intended use of the personal care composition, which is typically between pH 3 and pH 9). Particularly suitable cationic deposition polymers for use herein include KG 30 M and LR 30M, available from Dow.

In some aspects, the cationic deposition polymer can contain cationic nitrogen-containing moieties such as quaternary ammonium or cationic protonated amino moieties. The cationic protonated amines can be primary, secondary, or tertiary amines, depending upon the particular species and the selected pH of the composition. Anionic counterions can be used in association with the cationic polymers as long as the polymers remain soluble in water, in the composition, and in a coacervate phase of the composition. Examples of suitable counterions include halide counterions (e.g., chloride, fluoride, bromide, iodide). Non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers can include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers can include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as polyquaternium 39), and terpolymers of acrylic acid with methacrylamidopropyl trimethylammonium chloride and methylacrylate (referred to in the industry by CTFA as Polyquaternium 47). In certain embodiments, suitable cationic substituted monomers include cationic substituted dialkylaminoalkyl acrylamides, dialkylaminoalkyl methacrylamides, and combinations thereof. Generally, cationic monomers can conform to the formula III:

Formula III wherein $R^{14}$ is hydrogen, methyl or ethyl; each of $R^{15}$, $R^{16}$ and $R^{17}$ are independently hydrogen or a short chain alkyl having from 1 to 8 carbon atoms, or from 1 to 5 carbon atoms, or from 1 to 2 carbon atoms; n is an integer having a value of from 1 to 8, or 1 to 4; and X is a counterion. The nitrogen attached to $R^{15}$, $R^{16}$ and $R^{17}$ can be a protonated amine (primary, secondary or tertiary), but can also be a quaternary ammonium wherein each of $R^{15}$, $R^{16}$ and $R^{17}$ are alkyl groups. In certain embodiments, the cationic monomer can be polymethyacrylamidopropyl trimonium chloride, available under the trade name POLYCARE 133, from Rhone-Poulenc, Cranberry, N.J., U.S.A. In certain embodiment, copolymers of the cationic monomer are also suitable. In such embodiments, the charge density of the total copolymer can be 2.0 meq/g to 4.5 meq/g.

Other cationic polymers are also suitable including polysaccharide polymers, such as cationic cellulose derivatives and cationic starch derivatives. Suitable cationic polysaccharide polymers include those which conform to Formula IV:

Formula IV wherein A is an anhydroglucose residual group, such as a starch or cellulose anhydroglucose residual; $R^{18}$ is an alkylene oxyalkylene, polyoxyalkylene, or hydroxyalkylene group, or combination thereof; $R^{19}$, $R^{20}$, and $R^{21}$ are independently alkyl, aryl, alkylaryl, arylalkyl, alkoxyalkyl, or alkoxyaryl groups, wherein each group contains up to 18 carbon atoms, and the total number of carbon atoms for each cationic moiety (i.e., the sum of carbon atoms in $R^{19}$, $R^{20}$, and $R^{21}$) is 20 or less; and X is an anionic counterion.

In certain embodiments, a cationic cellulose polymer can be selected from the salts of hydroxyethyl cellulose reacted with trimethyl ammonium substituted epoxide, referred to in the industry (CTFA) as polyquaternium 10 and available from Amerchol Corp. (Edison, N.J., USA) in their Polymer LR, JR, and KG series of polymers. Other suitable cationic cellulose polymers can include polymeric quaternary ammonium salts of hydroxyethyl cellulose reacted with lauryl dimethyl ammonium-substituted epoxide referred to in the industry (CTFA) as polyquaternium 24. These materials are available from Amerchol Corp. under the tradename Polymer LM-200.

Other suitable cationic polymers can include cationic guar gum derivatives, such as guar hydroxypropyltrimonium chloride. Additional examples of suitable cationic guar gum derivatives can include the Jaguar series commercially available from Rhone-Poulenc Incorporated and the N-Hance series commercially available from Aqualon Division of Hercules, Inc. Additional details about cationic guar gum derivatives are disclosed in U.S. Pat. No. 6,930,078.

As can be appreciated, other cationic polymers known in the personal care industry are also suitable. For example, quaternary nitrogen-containing cellulose ethers are suitable. Examples of quaternary nitrogen-containing cellulose ethers are described in U.S. Pat. No. 3,962,418.

In certain embodiments, a synthetic cationic polymer or derivative thereof can be useful as a cationic polymer. Generally, such synthetic cationic polymers can be included at a concentration of 0.025% to 5%. Suitable synthetic cationic polymers can include polymers which are water-soluble or dispersible, are cationic, and are non-crosslinked. In certain embodiments, suitable polymers can be conditioning copolymers comprising: (i) one or more cationic monomer units; and (ii) one or more nonionic monomer units or monomer units bearing a terminal negative charge; wherein said copolymer has a net positive charge. In certain embodiments, the synthetic cationic polymers can have a cationic charge density of 0.5 meq/g to 10 meg/g and an average molecular weight of 1,000 da to 5,000,000 da. Non-limiting examples of suitable synthetic cationic deposition polymers are described in U.S. Publication No. 2003/0223951.

Other suitable cationic polymers include copolymers of etherified cellulose, guar and starch, some examples of which are described in U.S. Pat. No. 3,958,581. Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

When present in the composition, the cationic polymers should be soluble in the composition or soluble in a complex coacervate phase in the composition, which can be formed by interaction of the cationic polymer and a sulfate-free anionic, amphoteric or zwitterionic detersive surfactant. Complex coacervates of the cationic polymer can also be formed with other anionic charged materials in the personal care composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164.

Anti-Dandruff Actives

The personal care composition herein contains an anti-dandruff agent. Suitable anti-dandruff agents can include pyridinethione salts, azoles, selenium sulfide, particulate sulfur, and mixtures thereof. Such anti-dandruff particulate should be physically and chemically compatible with the essential components of the composition, and should not otherwise unduly impair product stability, aesthetics or performance. In certain embodiments, a personal care composition can include a cationic polymer to enhance deposition of an anti-dandruff active. Particularly suitable antidandruff actives include zinc pyrithione, piroctone olamine, azoxystrobin, sulfur, salicylic acid and combinations of these.

a. Pyridinethione Salts

In certain embodiments, an anti-dandruff agent can be a pyridinethione particulate such as a 1-hydroxy-2-pyridinethione salt. The pyridinethione may be present at 0.1% to 4% (e.g., 0.1% to 3%, 0.1% to about 2% or 0.3% to 2%). Suitable pyridinethione salts include those formed from heavy metals such as zinc, tin, cadmium, magnesium, aluminum and zirconium, the zinc salt of 1-hydroxy-2-pyridinethione (known as "zinc pyridinethione" or "ZPT"), alternatively 1-hydroxy-2-pyridinethione salts in platelet particle form, wherein the particles have an average size of up to 20 μm, (up to 5 μm, or 2.5 μm). Salts formed from other cations, such as sodium, can also be suitable. Pyridinethione anti-dandruff agents are further described in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate, that the growth or re-growth of hair may be stimulated or regulated, or both, or that hair loss may be reduced or inhibited, or that hair may appear thicker or fuller.

b. Other Anti-Microbial Actives

In addition to the anti-dandruff active selected from polyvalent metal salts of pyrithione, a personal care composition can further include one or more anti-fungal or anti-microbial actives in addition to the metal pyrithione salt actives. Suitable anti-microbial actives include coal tar, beta hydroxy acids, selenium sulfide, sulfur, azoxystrobin, whitfield's ointment, castellani's paint, aluminum chloride, gentian violet, octopirox (piroctone olamine), ciclopirox olamine, undecylenic acid and its metal salts, potassium permanganate, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, SENSIVA™ SC-50, ELESTAB™ HP-100, azelaic acid, lyticase, iodopropynyl butylcarbamate (IPBC), azoles, isothiazalinones, and combinations thereof.

In particular examples, the personal care compositions herein may contain 0.02% to 10% of azoxystrobin; 0.1% to 2% piroctone olamine; 0.1% to 10% beta hydroxy acid (e.g., salicylic acid); 0.01% to 5% of an azole (e.g., benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole); and/or 0.1% to 4% selenium sulfide; 0.1% to 5% sulfur. In still other examples, combinations of antidandruff and/or antimicrobial compounds such as octopirox and zinc pyrithione combinations, pine tar and sulfur combinations, salicylic acid and zinc pyrithione combinations, octopirox and climbazole combinations, and salicylic acid and octopirox combinations, and mixtures thereof.

Humectant

A personal care composition can also include a humectant to lower the rate of water evaporation from hair or skin. Suitable humectants can include polyhydric alcohols, water soluble alkoxylated nonionic polymers, and mixtures thereof. Suitable polyhydric alcohols can include glycerin, sorbitol, propylene glycol, butylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Suitable water soluble alkoxylated nonionic polymers can include polyethylene glycols and polypropylene glycols having a molecular weight of up to about 1000 such as those with CTFA names PEG-200, PEG-400, PEG-600, PEG-1000, and mixtures thereof. The humectants, when included, can be present at 0.1% to 20% (e.g., 0.5% to about 5%).

Other Optional Components

As can be appreciated, a personal care composition can include still further optional components. For example, amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

In certain embodiments, a personal care composition can optionally include pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions can also include antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

In certain embodiments, one or more stabilizers and preservatives can be included. For example, one or more of trihydroxystearin, ethylene glycol distearate, citric acid, sodium citrate dihydrate, a preservative such as: kathon, sodium chloride, sodium benzoate, and ethylenediaminetetraacetic acid ("EDTA") can be included to improve the lifespan of a personal care composition. Particularly suitable is sodium benzoate at a level of 0.10% to 0.45%. The personal care composition may also include citric acid at 0.5% to 1%. The sodium benzoate and the citric acid can be added to the personal care composition alone or in combination.

Chelants can also be included to scavenge metal and reduce hair damage caused by exposure to UV radiation. Examples of suitable chelants include histidine and N,N' ethylenediamine disuccinic acid ("EDDS").

Method of Use

The personal care compositions described herein can be used in a conventional manner for cleansing and conditioning of hair or skin. Generally, a method of treating hair or skin can include applying the personal care composition to the hair or skin. For example, an effective amount of the personal care composition can be applied to the hair or skin, which has been wetted with water, and then the composition can be rinsed off. Effective amounts can generally range from about 1 g to about 50 g in certain embodiments, and from about 1 g to about 20 g in certain embodiments. Application to the hair typically includes working the composition through the hair such that most or all of the hair is contacted with the composition.

In certain embodiments, a method for treating the hair or skin can include the steps of: (a) wetting the hair or skin with water; (b) applying an effective amount of the personal care composition to the hair or skin, and (c) rinsing the applied areas of skin or hair with water. These steps can be repeated as many times as desired to achieve the desired cleansing and conditioning benefit.

In certain embodiments, a personal care composition as described herein can be used to treat damaged hair. Damaged hair can include hair permed hair, oxidatively colored hair, and mechanically damaged hair.

The personal care compositions can be used as liquids, solids, semi-solids, flakes, gels, in a pressurized container with a propellant added, or used in a pump spray form. The viscosity of the product may be selected to accommodate the form desired.

METHODS

Stability

This method involves visually inspecting a test composition for signs of instability (e.g., creaming, precipitation, phase separation, and sedimentation), which are well-recognized in the art. Two test samples of the composition (~50 g) are each placed in a separate transparent container. The containers are then covered with a suitable lid to inhibit evaporation and contamination. One container is placed in a 5° C. temperature-controlled room and the other is placed in a and 40° C. temperature-controlled room. After one month, the samples are removed from the temperature-controlled rooms and allowed to equilibrate to room temperature (e.g., 1 hour). Next, the sample are visually inspected to observe any changes in physical properties of the composition (e.g., phase separation or precipitation). Samples that have no observable signs of instability are identified with a "Yes" to indicate that the composition is phase stable. Samples that exhibit visual signs of instability are identified with a "No" to indicate that the composition is not phase stable.

Viscosity Measurement

This method provides a way to measure the viscosity of a composition or material using a suitable rheometer (e.g., Cone/Plate Controlled Stress Brookfield Rheometer R/S Plus or equivalent). A 75 mm diameter cone with 1° angle (e.g., Spindle C-75-1) is used. The viscosity of a liquid sample is determined using a steady state flow experiment at a constant shear rate of $2\ s^{-1}$ and temperature of 26.7° C. The sample size is 3 ml and the total measurement reading time is 3 minutes.

Rheology Measurement

This method provides a way to determine low-shear yield stress using a suitable rheometer (e.g., a TRIOS brand rheometer or equivalent). The rheometer is configured to test the sample composition at 26.7° C. using a 60 mm (diameter) cone with a 2.005 degree angle and a Peltier aluminum plate. The sample gap is set at 52 μm, and the sample is run via a logarithmic sweep from 10 to $1.0 \times 10^{-4}\ s^{-1}$. A Herschel Bulkley analysis of the shear stress curve from $10^{-4}$ Pa to $10^{-2}$ Pa is performed, e.g., using the manufacturer's software installed on the Trios Rheometer, to determine the low-shear yield stress in Pascals (Pa).

In Vivo Scalp Deposition.

This method provides a way to determine the amount of anti-dandruff (AD) active deposited on the scalp of a test subject. A trained cosmetician applies approximately 5 g of a control shampoo to the test subject's hair on the right or left side of the head, and then washes the test subject's hair on that half using a conventional hair washing technique (e.g., lather for 60 seconds and then rinse until all lather is out of the hair). The trained cosmetician next applies approximately 5 g of the test shampoo, containing the anti-dandruff active to the other half of the test subject's head, and then washes the test subject's hair on that half using the conventional hair washing technique. The hair is then parted on the control side and the test side of the scalp to allow an open-ended glass cylinder to be held on the surface of the scalp to form a liquid-impermeable seal. An aliquot of an ethanol extraction solvent is added to the open end of the cylinder that is opposite the end held against the scalp. The solvent is agitated by carefully shaking or rocking the cylinder without breaking the liquid-impermeable seal. The extraction solvent is recovered using conventional means (e.g., suction).

The concentration of the anti-dandruff agent in the ethanol extraction solvent is measured by HPLC. Quantitation is made by reference to a standard curve. The concentration detected by HPLC is converted into an amount collected in grams by using the concentration multiplied by volume. The deposition efficiency can be calculated using the following equation. The area of the scalp extracted in each case is held constant:

$$\text{Deposition efficiency} = \frac{\text{mass agent deposited by example formula}}{\text{mass agent deposited by control formula}}$$

Sample calculation for deposition efficiency, where:
Mass of AD active deposited by example formula=7.8 ug
Mass of AD active deposited by control formula=1.3 ug $$\text{Deposition efficiency} = \frac{7.8}{1.3}$$

$$\text{Deposition efficiency} = 6X$$

EXAMPLES

Table 1 below provides examples of inventive and comparative personal care compositions described herein. Of course, these examples are not intended to be limiting. Other modifications can be undertaken by the skilled artisan without departing from the spirit and scope of this invention. The exemplified embodiments of the inventive composition provide suitable cleaning benefits to hair without the use of a harsh sulfate-based surfactant.

The personal care compositions illustrated in the following Examples are prepared by conventional formulation and mixing methods. The pH can be measured with a Thermo Scientific Orion Star A321 pH meter or equivalent that is calibrated prior to use. Other properties of the composition are determined according to the methods described herein.

TABLE 1

| Ingredients | 1 | 2 | 3 | 4 | 5 | 6 |
|---|---|---|---|---|---|---|
| | | | Wt % | | | |
| Sodium cocoyl alaninate [1] | 9.16 | 9.16 | 9.16 | 9.16 | 9.16 | 9.16 |
| Glyceryl caprylate/caprate [2] | 5 | 5 | 5 | 5 | 5 | 5 |
| Polyquaternium10 [3] | | | | | | 0.6 |
| Polyquaternium10 [4] | | | | | | |
| Guar hydroxypropyltrimonium chloride [5] | | | 0.6 | 0.3 | 0.6 | |
| Piroctone olamine | 0.5 | 0.5 | 0.5 | 0.5 | 0.25 | 0.5 |
| Sodium benzoate | 0.25 | 0.25 | 0.25 | 0.25 | 0.25 | 0.25 |
| Perfume | 1 | 1 | 1 | 1 | 1 | 1 |

TABLE 1-continued

| | | | | | | |
|---|---|---|---|---|---|---|
| Citric acid | To pH 5.0-6.0 | To pH 5.0-6.0 | To pH 5.0-6.0 | To pH 5.0-6.0 | To pH 5.0-6.0 | To pH 5.0-6.0 |
| DI Water | Q.S. | Q.S. | Q.S. | Q.S. | Q.S. | Q.S. |
| NaCl added | 0 | 0 | 0 | 0 | 0 | 0 |
| Product appearance | Opaque | Opaque | Opaque | Opaque | Opaque | Opaque |
| Phase stable at 40° C. | Yes | Yes | Yes | Yes | Yes | Yes |
| Phase stable at 5° C. | Yes | Yes | Yes | Yes | Yes | Yes |
| Viscosity, mPa-s | 346 | 3098 | 3225 | 2294 | 3045 | 4066 |
| Low-shear yield stress | 0.62 | 1.47 | 1.43 | 0.41 | NA | 1.45 |
| pH | 5.7 | 5.27 | 5.6 | 5.5 | 5.5 | 5.5 |
| Vesicles | Yes | Yes | Yes | Yes | Yes | Yes |
| Deposition efficiency | 0.77× | NA | 2.2× | 1.6× | 1.1× | 6.0× |

| Ingredients | 7 | 8 | 9 | 10 | 11 | 12 | 13 |
|---|---|---|---|---|---|---|---|
| | | | | Wt% | | | |
| Sodium cocoyl alaninate [1] | 9.16 | 9.16 | 9.16 | 7.6 | 7.6 | 9.16 | |
| Sodium cocoyl alaninate [6] | 5 | | | | | | 12 |
| Glyceryl caprylate/caprate [2] | | 10 | 10 | 5 | 5 | 2.5 | 2.5 |
| Polyquaternium10 [3] | | | 0.6 | | | 0.6 | 0.6 |
| Polyquaternium10 [4] | 0.6 | 0.6 | | 0.6 | | | |
| Lauric acid | | | | | | 2.5 | 2.5 |
| Guar hydroxypropyltrimonium chloride[5] | | | | | 0.6 | | |
| Piroctone olamine | 0.5 | 0.5 | 0.5 | 0.5 | 0.5 | 0.5 | 0.5 |
| Sodium benzoate | 0.25 | 0.25 | 0.25 | 0.25 | 0.25 | 0.25 | 0.25 |
| Perfume | 1 | 1 | 1 | 1 | 1 | 1 | 1 |
| Citric acid | To pH 5.0-6.0 | To pH 5.0-6.0 | To pH 5.0-6.0 | To pH 5.0-6.0 | To pH 5.0-6.0 | To pH 5.0-6.0 | To pH 5.0-6.0 |
| DI Water | Q.S. | Q.S. | Q.S. | Q.S. | Q.S. | Q.S. | Q.S. |
| NaCl added | 0 | 0 | 0 | 0 | 0 | 0 | 2 |
| Measurements | | | | | | | |
| Product appearance | Opaque | Opaque | Opaque | Opaque | Opaque | Opaque | Opaque |
| Phase stable 40° C. | Yes | Yes | Yes | Yes | Yes | Yes | Yes |
| Phase stable at 5° C. | Yes | Yes | Yes | Yes | Yes | Yes | Yes |
| Viscosity, mPa-s | 10925 | 18628 | 12549 | 7164 | 3559 | 6720 | 5388 |
| Low-shear yield stress (Pa) | 1.92 | 3.56 | 3.0 | 0.58 | NA | 1.2 | 4.8 |
| pH | 5.7 | 5.8 | 5.8 | 5.5 | 5.5 | 5.5 | 5.35 |
| Vesicles | Yes | Yes | Yes | Yes | Yes | Yes | Yes |
| Deposition efficiency | 2.5× | 2× | NA | 2.6× | 3.6× | NA | NA |

| Ingredients | 14 | 15 | 16 | 17 | 18 | 19 | 20 |
|---|---|---|---|---|---|---|---|
| | | | | Wt % | | | |
| Sodium cocoyl alaninate [1] | 9.16 | 9.16 | 9.16 | 9.16 | 9.16 | 9.16 | 9.16 |
| Glyceryl caprylate/caprate [2] | 5 | 5 | | 5 | 5 | 5 | 5.5 |
| Glyceryl caprylate/caprate [7] | | | 5 | | | | |
| Polyquaternium10 [3] | | 0.25 | | | | | |
| Polyquaternium 10 [4] | 0.25 | | 0.6 | 0.6 | | | 0.6 |
| Guar hydroxypropyltrimonium chloride [5] | | | | | 0.6 | 0.6 | |
| Piroctone olamine | 0.5 | 0.5 | 0.5 | | | | |
| Zinc pyrithione | | | | 1 | 1 | 2 | 1 |
| Sodium benzoate | 0.25 | 0.25 | 0.25 | 0.25 | 0.25 | 0.25 | 0.25 |
| Perfume | 1 | 1 | 1 | 1 | 1 | 1 | 1 |
| Citric acid | To pH 5.0-6.0 | To pH 5.0-6.0 | To pH 5.0-6.0 | To pH 5.0-6.0 | To pH 5.0-6.0 | To pH 5.0-6.0 | To pH 5.0-6.0 |
| DI Water | Q.S. | Q.S. | Q.S. | Q.S. | Q.S. | Q.S. | Q.S. |
| NaCl added | 0 | 0 | 0 | 0 | 0 | 0 | 0 |
| Measurements | | | | | | | |
| Product appearance | Opaque | Opaque | Opaque | Opaque | Opaque | Opaque | Opaque |
| Phase stable 40° C. | Yes | Yes | No | Yes | Yes | Yes | Yes |
| Phase stable at 5° C. | Yes | Yes | Yes | Yes | Yes | Yes | Yes |
| Viscosity, mPa-s | 3435 | 4382 | 3818 | 10448 | 8981 | 9774 | 11699 |
| Low-shear yield stress (Pa) | 0.5 | 0.43 | 0.087 | 1.69 | 1.8 | 2.1 | 6.07 |

TABLE 1-continued

| | | | | | | | |
|---|---|---|---|---|---|---|---|
| pH | 5.12 | 5.3 | 5.5 | 5.6 | 5.6 | 5.5 | 5.4 |
| Vesicles | Yes | Yes | Yes | Yes | Yes | Yes | yes |
| Deposition efficiency | NA | NA | NA | 20× | 4.7× | 10.8× | NA |

[1] EVERSOFT ACS-30S (~5% NaCl) from Sino Lion
[2] STEPAN MILD GCC from Stepan Company
[3] KG30M from Dow
[4] LR30M from Dow
[5] JAGUAR EXCEL from Solvay
[6] EVERSOFT ACS (~1% NaCl) from Sino Lion
[7] CAPMUL MCM from Abitec Corp.

TABLE 2

Comparative Examples

| Ingredients | Comp 1. | Comp 2. | Comp 3. | Comp 4. |
|---|---|---|---|---|
| | | Wt % | | |
| Sodium cocoyl alaninate [1] | 5 | 9.16 | 9.16 | |
| Sodium laureth-3 sulfate | | | | 12 |
| Glyceryl caprylate/caprate [2] | 5 | 2.5 | | 5 |
| Polyquaternium10 [3] | | 0.6 | 0.6 | 0.6 |
| Guar hydroxypropyltrimonium chloride [4] | 0.6 | | | |
| Lauric acid | | | 4 | |
| Piroctone olamine | 0.5 | 0.5 | 0.5 | 0.5 |
| Sodium benzoate | 0.25 | 0.25 | 0.25 | 0.25 |
| Perfume | 1 | 1 | 1 | 1 |
| Citric acid | To pH 5.0-6.0 | To pH 5.0-6.0 | To pH 5.0-6.0 | To pH 5.0-6.0 |
| DI Water | Q.S. | Q.S. | Q.S. | Q.S. |
| NaCl added | 0 | 0 | 1.5 | 0 |
| Measurements | | | | |
| Product appearance | Opaque | Opaque | Opaque | Opaque |
| Phase stable at 40° C. | No | No | Yes | No |
| Phase stable at 5° C. | No | No | No | No |
| Viscosity mPa-s | 1398 | 3123 | 6211 | 823 |
| Low-shear yield stress (Pa) | NA | 0.23 | 2.3 | 0.047 |
| pH | 5.7 | 5.5 | 5.4 | 4.4 |
| Vesicles | Yes | Yes | Yes | Yes |
| Deposition efficiency | NA | NA | 4.3X | NA |

[1] EVERSOFT ACS-30S (~5% NaCl) from Sino Lion
[2] STEPAN MILD GCC from Stepan Company
[3] KG30M from Dow
[4] JAGUAR EXCEL from Solvay

TABLE 3

Zinc Pyrithione and Piroctone Olamine Controls

| Ingredients | 21 | 22 |
|---|---|---|
| | Wt % | |
| Sodium laureth-3 sulfate | 6 | 8 |
| Sodium lauryl sulfate | 7 | 7 |
| Cocamidopropyl betaine | 1 | 2 |
| Glycol distearate | 2.5 | 1.5 |
| Guar hydroxypropyltrimonium chloride [1] | 0.23 | |
| Guar hydroxypropyltrimonium chloride [2] | | 0.25 |
| Piroctone olamine [3] | | 0.5 |
| Zinc pyrithione [4] | 1 | |
| Zinc carbonate | 1.61 | |
| Sodium benzoate | | 0.25 |
| Tetrasodium EDTA | | 0.16 |
| Methylchloroisothiazolinone/methylisothiazolinone [5] | 0.03 | 0.03 |
| Sodium xylenesulfonate | | QS |
| Perfume | | 0.85 |
| Dimethicone [6] | 0.8 | |
| Dimethiconol and Dimethicone DM5500 [7] | | 0.5 |
| Citric acid | NA | pH 5.5-6.5 |
| HCL | pH 6.7-7.3 | |
| Di water | Q.S. | Q.S. |
| NaCl added | 1.22 | 0.5 |
| Product appearance, visual | Opaque | Opaque |
| Phase Stable 40° C. | Yes | Yes |
| Phase Stable at 5° C. | Yes | Yes |
| Viscosity, mPa-s | 8908 | 9306 |
| Low-shear yield stress (Pa) | 0.04 | 0.009 |
| pH | 7 | 6.18 |
| Vesicles | No | No |
| Depo efficiency | 1X | 1X |

[1] N Hance 3271 from Ashland
[2] N Hance 3196 from Ashland
[3] Piroctone olamine from Clariant Specialty Chemicals
[4] Zinc pyrithione from Lonza
[5] Kathon from Rohm and Haas
[6] DC330M from Dow
[7] DM5500 from Whacker The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) sodium cocoyl alaninate, wherein the sodium cocoyl alaninate is present at 5% to 20% by weight of the composition;
   b) a glyceryl ester, wherein the glyceryl ester is present at 1% to 20% by weight of the composition, wherein the glyceryl ester is glyceryl caprate, glyceryl caprylate, or a mixture thereof, wherein the total amount of glyceryl ester ranges from 1% to 20% by weight of the composition; wherein the composition comprises a weight ratio of sodium cocoyl alaninate to glyceryl ester is between 3:1 to 3:2;
   c) from about 0.1% to about 2% of an antidandruff agent selected from the group consisting of zinc pyrithione, piroctone olamine and mixtures thereof;
   d) a liquid carrier, wherein the personal care composition is substantially free of sulfated surfactants
   e) from about 0.1% to about 3% of a cationic deposition polymer selected from the group consisting of guar, cellulose, derivatives of these and combinations thereof.

2. The personal care composition of claim 1, wherein the sodium cocoyl alaninate is present at about 7% to about 20%.

3. The personal care composition of claim 1, where the glyceryl ester is present at about 2.5% to about 10%.

4. The personal care composition of claim 1, further comprising polyglyceryl 2-triisostearate.

5. The personal care composition of claim 3, wherein the glyceryl ester is a mixture of glyceryl caprylate and glyceryl caprate and is substantially free of polyethylene glycol, ethylene oxide/propylene oxide, and nitrogen.

6. The personal care composition of claim 1, wherein the personal care composition has a low-shear yield stress value of from about 0.005 Pa to 20 Pa.

7. The personal care composition of claim 1, further comprising from about 0.1% to about 2.5% lauric acid.

8. The personal care composition of claim 1, wherein the personal care composition is stable at 5° C. and 40° C., according to a Stability method for visually inspecting the personal care composition for creaming, precipitation, phase separation, and sedimentation.

9. The personal care composition of claim 1, wherein the cationic deposition polymer has a charge density of about 0.7 meq/g to about 2.0 meq/g.

10. The personal care composition of claim 1, wherein the cationic deposition polymer has weight average molecular weight of from about 500,000 daltons to about 2,000,000 daltons.

11. The personal care composition of claim 1, wherein the composition comprises less than about 3% of added salt.

12. The personal care composition of claim 1, wherein the personal care composition is a shampoo.

13. The personal care composition of claim 1, wherein the personal care composition is substantially free of silicones.

14. The personal care composition of claim 1, wherein the composition has a pH of from about 5 to about 6.

* * * * *